United States Patent
Gemborys

(10) Patent No.: US 9,801,983 B2
(45) Date of Patent: Oct. 31, 2017

(54) MEDICAL DEVICES FOR DELIVERING A BIOACTIVE TO A POINT OF TREATMENT AND METHODS OF MAKING MEDICAL DEVICES

(71) Applicant: Cook Medical Technologies LLC, Bloomington, IN (US)

(72) Inventor: Colleen Gemborys, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 137 days.

(21) Appl. No.: 14/971,273

(22) Filed: Dec. 16, 2015

(65) Prior Publication Data

US 2016/0175494 A1  Jun. 23, 2016

Related U.S. Application Data

(60) Provisional application No. 62/093,684, filed on Dec. 18, 2014.

(51) Int. Cl.
*A61L 31/10* (2006.01)
*A61L 31/16* (2006.01)
*A61L 31/14* (2006.01)

(52) U.S. Cl.
CPC .............. *A61L 31/16* (2013.01); *A61L 31/10* (2013.01); *A61L 31/146* (2013.01); *A61L 2420/02* (2013.01)

(58) Field of Classification Search
CPC ......... A61L 31/16; A61L 31/146; B05C 11/02
USPC ....................................... 427/2.1, 2.24, 2.25
See application file for complete search history.

(56) References Cited

U.S. PATENT DOCUMENTS

| | | | |
|---|---|---|---|
| 4,292,972 A | 10/1981 | Pawelchak et al. | |
| 4,842,575 A * | 6/1989 | Hoffman, Jr. .............. | A61F 2/06 106/146.1 |
| 5,298,276 A * | 3/1994 | Jayaraman ................ | A61F 2/06 427/2.25 |
| 5,312,642 A * | 5/1994 | Chesterfield ...... | A61B 17/06166 427/2.31 |
| 5,516,395 A | 5/1996 | Anhauser et al. | |
| 5,733,337 A | 3/1998 | Carr, Jr. et al. | |
| 6,180,162 B1 * | 1/2001 | Shigeru .................. | A01N 25/34 427/11 |
| RE39,192 E | 7/2006 | MacPhee et al. | |
| 7,229,959 B1 | 6/2007 | Drohan et al. | |

(Continued)

FOREIGN PATENT DOCUMENTS

WO    WO2013123018    8/2013

*Primary Examiner* — Cachet Sellman
(74) *Attorney, Agent, or Firm* — Buchanan Van Tuinen LLC

(57) ABSTRACT

Methods of making medical devices are described. A method of making a medical device for delivering a bioactive includes preparing a suitable solution comprising the bioactive; placing a vessel containing the solution over a substrate comprising a biocompatible foam and defining open cells; initiating flow of the solution from the vessel and toward the substrate such that the solution exits the vessel and contacts the substrate; and maintaining flow of the solution for an amount of time sufficient to achieve a desired volume of the solution within the substrate. Medical devices made by the methods are also described.

20 Claims, 9 Drawing Sheets

(56) References Cited

U.S. PATENT DOCUMENTS

| | | |
|---|---|---|
| 8,029,560 B2 | 10/2011 | Bates et al. |
| 8,313,521 B2 | 11/2012 | Ruane et al. |
| 8,329,219 B2 | 12/2012 | Farrell et al. |
| 8,388,994 B1 | 3/2013 | Scheer et al. |
| 8,439,942 B2 | 5/2013 | Moran et al. |
| 8,465,516 B2 | 6/2013 | Pavcnik et al. |
| 8,501,229 B2 | 8/2013 | Faucher et al. |
| 8,529,939 B2 | 9/2013 | Masters et al. |
| 8,557,277 B2 | 10/2013 | Virkler et al. |
| 8,623,046 B2 | 1/2014 | Sturtevant |
| 8,658,196 B2 | 2/2014 | Janis |
| 8,741,354 B2 | 6/2014 | Johnson et al. |
| 8,882,850 B2 | 11/2014 | Hiles et al. |
| 2003/0229393 A1* | 12/2003 | Kutryk .................. A61K 31/721 623/1.46 |
| 2007/0148243 A1 | 6/2007 | Bates |
| 2008/0057101 A1 | 3/2008 | Roorda |
| 2009/0123516 A1 | 5/2009 | Agrawal et al. |
| 2009/0317469 A1 | 12/2009 | Johnson et al. |
| 2009/0318934 A1 | 12/2009 | Johnson et al. |
| 2009/0326577 A1 | 12/2009 | Johnson et al. |
| 2010/0063459 A1 | 3/2010 | Preiss-Bloom et al. |
| 2010/0106178 A1 | 4/2010 | Obermiller et al. |
| 2010/0221310 A1 | 9/2010 | Virkler |
| 2012/0226211 A1 | 9/2012 | Preiss-Bloom et al. |
| 2013/0274219 A1 | 10/2013 | Nguyen et al. |
| 2014/0180398 A1 | 6/2014 | Milner et al. |
| 2014/0315847 A1 | 10/2014 | Peck et al. |

\* cited by examiner

MEDICAL DEVICES FOR DELIVERING A BIOACTIVE TO A POINT OF TREATMENT AND METHODS OF MAKING MEDICAL DEVICES

FIELD

The disclosure relates generally to the field of medical devices. More particularly, the disclosure relates to the field of medical devices suitable for use in delivery of a bioactive agent to a point of treatment in or on the body of an animal, such as a human being, and methods of making such medical devices.

BACKGROUND

Cancer is a leading cause of death worldwide. Current treatments for many cancers include systemic administration of bioactive agents that have negative side effects and that can significantly impact quality of life. Local delivery of bioactive agents directly to a point of treatment may provide a route of administration that avoids the side effects and quality of life implications associated with systemic delivery of cancer treatment agents and other bioactive agents. The art does not provide, however, suitable medical devices for achieving suitable local dosages that while avoiding systemic spread.

A need exists, therefore, for improved medical devices for delivering a bioactive to a point of treatment, and for methods of making such medical devices.

BRIEF SUMMARY OF SELECTED EXAMPLES

Several methods of making medical devices are described and illustrated herein. An example method comprises preparing a solution comprising a bioactive; placing a vessel containing the solution over a substrate comprising a biocompatible foam defining a plurality of cells; initiating flow of the solution toward the substrate such that the solution exits the vessel and contacts the substrate; and maintaining flow of the solution for an amount of time sufficient to achieve a desired volume of the solution within the substrate.

Another example method comprises preparing a water-based solution comprising a bioactive; placing a vessel containing the solution over a substrate comprising a biocompatible foam formed of an expanded natural material and defining a plurality of cells; initiating flow of the solution from the vessel and toward the substrate such that the solution exits the vessel and contacts the substrate; massaging the substrate to facilitate entry of the solution into the substrate; and maintaining flow of the solution for an amount of time sufficient to achieve a desired volume of the solution within the substrate.

Another example method comprises preparing a water-based solution comprising a bioactive; placing a vessel containing the solution over a substrate comprising a biocompatible foam formed of expanded small intestine submucosa and defining a plurality of cells; initiating flow of the solution from the vessel and toward the substrate such that the solution exits the vessel and contacts the substrate; massaging the substrate to facilitate entry of the solution into the substrate; maintaining flow of the solution for an amount of time sufficient to achieve a desired volume of the solution within the substrate; and drying the substrate.

An example medical device comprises a medical device made by an example method.

Additional understanding of the claimed medical devices and methods can be obtained by reviewing the description of selected examples, below, with reference to the appended drawings.

DETAILED DESCRIPTION OF SELECTED EXAMPLES

The following detailed description and appended drawings describe and illustrate various examples of the invention. The description and drawings serve to enable one skilled in the art to make and use the inventive methods; they are not intended to limit the scope of the invention or the protection sought in any manner. The invention is capable of being practiced or carried out in various ways. As such, the language used herein is intended to be given the broadest possible scope and meaning; and the examples described herein are exemplary in nature and not exhaustive.

Relevant background information is available in U.S. Pat. No. 8,658,196 to Janis on Feb. 25, 2014 for "GRAFT MATERIALS AND METHODS FOR STAGED DELIVERY OF BIOACTIVE COMPONENTS" and United States Published Application No. 2014/0180398 to Milner et al. for "BIOABSORBABLE MEDICAL DEVICES AND METHODS OF USE THEREOF", the contents of which are expressly incorporated into this disclosure in their entirety.

Unless otherwise defined herein, scientific and technical terms used in connection with the invention shall have the meanings that are commonly understood by those of ordinary skill in the art. Further, unless otherwise required by context, singular terms shall include pluralities and plural terms shall include the singular.

The following definitions are used throughout the disclosure: the term 'bioactive' and grammatically related terms refer to a substance that has a biological effect in an animal.

Figure 1:
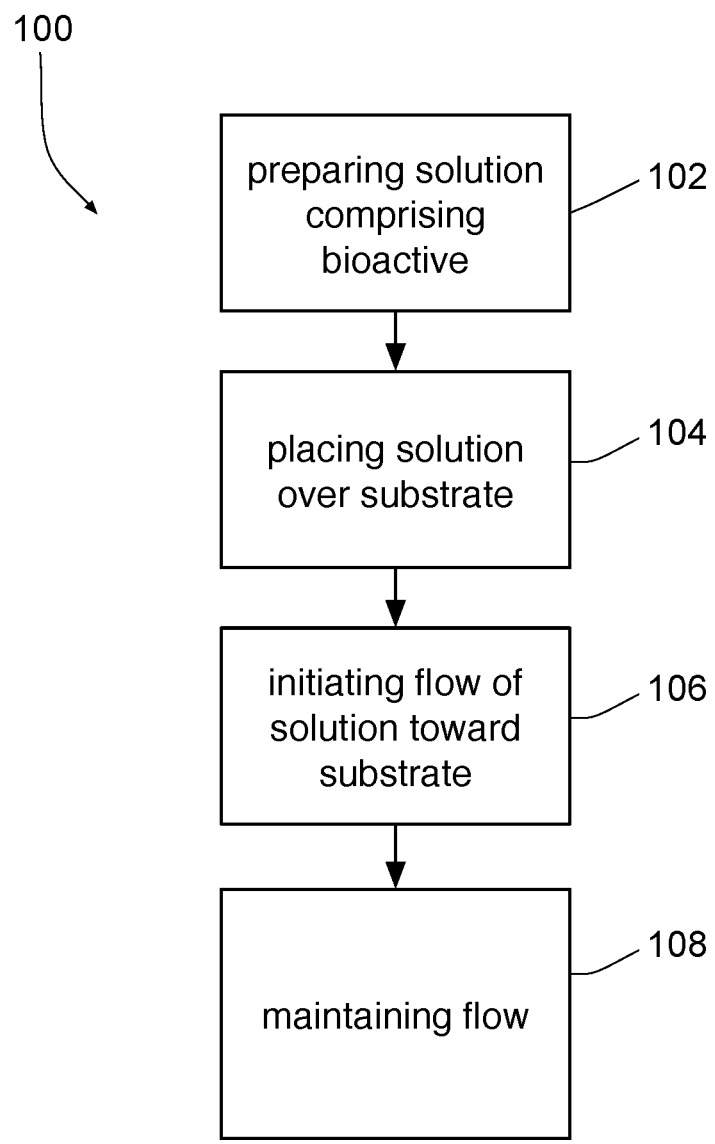
FIG. 1 is a schematic illustration of an example method of making a medical device for delivering a bioactive to a point of treatment.
Figure 2:
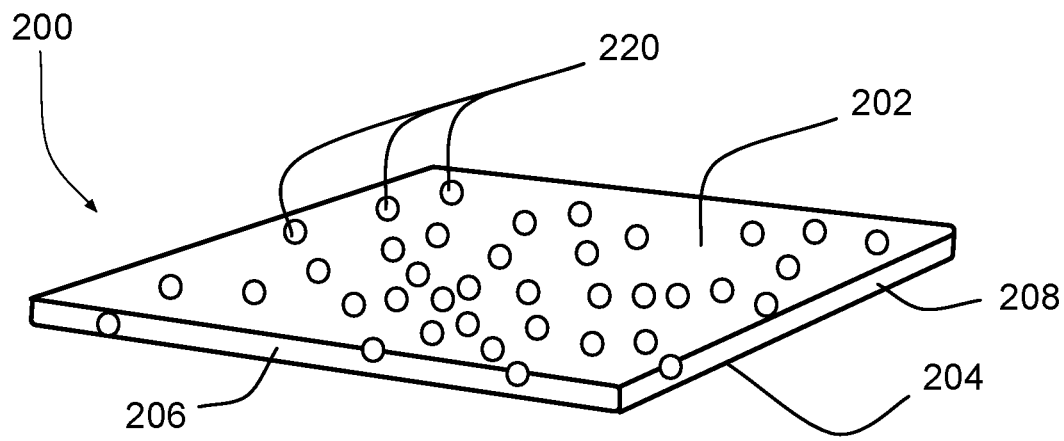
FIG. 2 is a perspective view of a substrate suitable for use in the example method.
Figure 3:
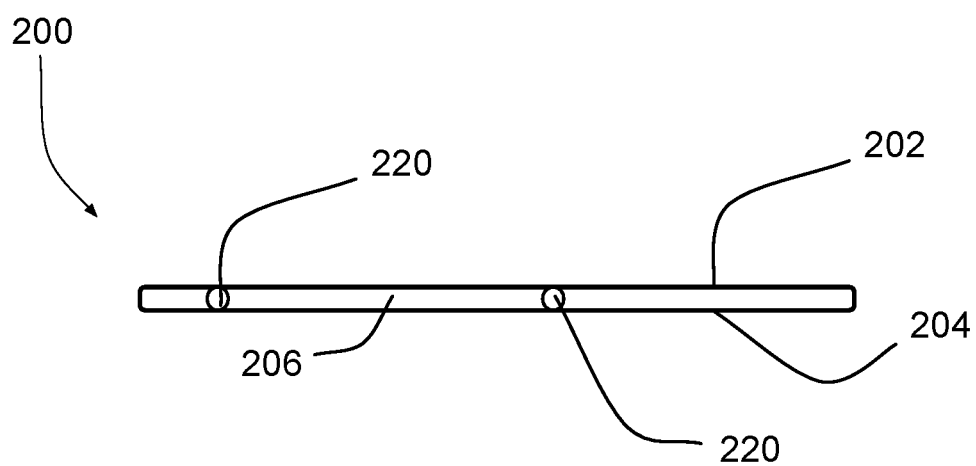
FIG. 3 is an elevation view of the substrate illustrate in FIG. 2.
Figure 4:
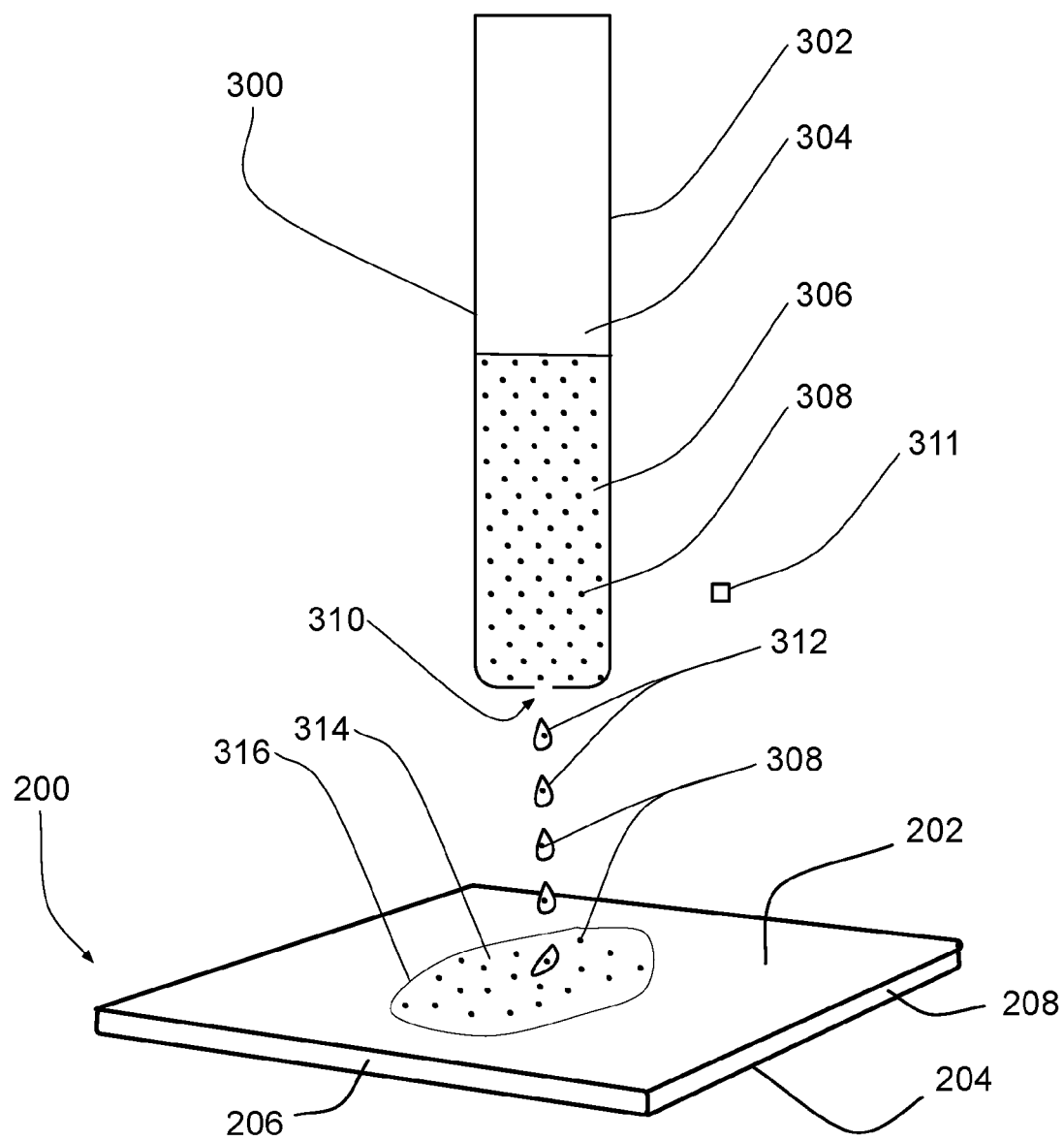
FIG. 4 is a perspective view of an apparatus and a substrate during performance of the example method.
Figure 5:
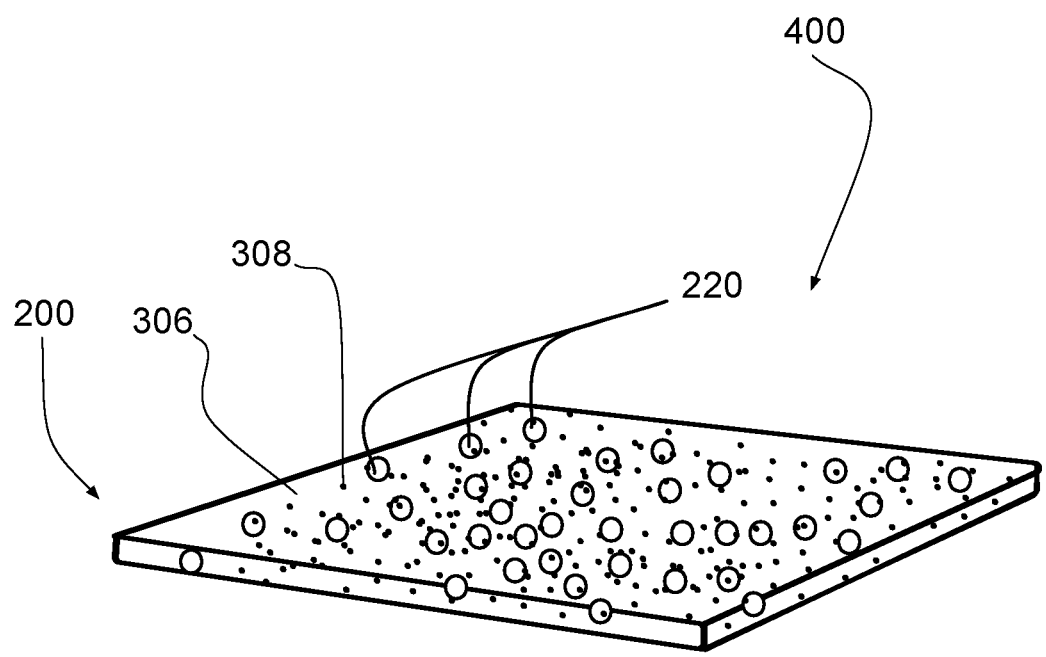
FIG. 5 is a perspective view of an example medical device produced by performance of the example method.

FIG. 1 schematically illustrates a first example method 100 of making a medical device for delivering a bioactive to a point of treatment. FIGS. 2 and 3 illustrate a substrate 200 suitable for use in the example method 10. FIG. 4 illustrates an apparatus 300 and the substrate 200 during performance of the example method 100. FIG. 5 illustrates a medical device 400 produced by performance of the example method.

As schematically illustrated in FIG. 1, the method 100 comprises preparing a solution comprising a bioactive 102; placing the solution over a substrate 104; initiating flow of the solution toward the substrate such that a portion of the solution contacts the substrate 106; and maintaining flow of the solution toward the substrate for an amount of time sufficient to achieve a desired volume of the solution within the substrate 108.

The bioactive used in a particular method can comprise a single bioactive, two bioactives, or a plurality of bioactives. When more than one bioactives are used, the bioactives can be mixed initially during the step 102 of preparing a solution, or the bioactives can be provided together, such as in a mixture or other suitable form, which can then be used in the step 102 of preparing a solution.

Any suitable bioactive can be used in the methods and medical devices described herein. The specific bioactive, or bioactives, selected for any particular method or medical device will depend upon several considerations, including the desired effect and the type of treatment and/or procedure in which the medical device is intended to be used. Examples of suitable bioactives include anti-cancer agents, such as paclitaxel, tamoxifen citrate, and Taxol® or derivatives thereof; anthracyclines, such as doxorubicin; pyrimidine analogs, such as 5-fluorouracil; nucleoside analogs, such as gemcitabine; platinum-based antineoplastics, such as cisplatin, carboplatin, oxaliplatin, satraplatin, picoplatin, nedaplatin, triplatin, and lipoplatin; immunosuppressive agents, such as cyclosporine and sirolimus; and other anti-cancer chemotherapeutic agents. Monoclonal and polyclonal antibodies can also be used as a bioactive in the methods and medical devices described herein. For example, recombinant humanized angiogenesis inhibiting monoclonal antibodies, such as Bevacizumab, are suitable. Also, chimeric monoclonal antibodies that inhibit epidermal growth factor receptor (EGFR), such as Cetuximab, are suitable. Also, anti-idiotype tumor antigen epitope mirroring monoclonal antibodies, such as Abagovomab, are suitable. Other examples of bioactives that can be used in the methods and medical devices include, but are not limited to, heparin, covalent heparin or another thrombin inhibitor, hirudin, hirulog, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof; a tyrosine-kinase inhibitor, such as Imatinib; a fibrinolytic agent; a vasospasm inhibitor; a calcium channel blocker, a nitrate, nitric oxide, a nitric oxide promoter or another vasodilator; an antimicrobial agent or antibiotic; aspirin, ticlopidine, a glycoprotein IIb/IIIa inhibitor or another inhibitor of surface glycoprotein receptors, or another antiplatelet agent; colchicine or another antimitotic, or another microtubule inhibitor, dimethylsulfoxide (DMSO), a retinoid or another antisecretory agent; cytochalasin or another actin inhibitor; or a remodeling inhibitor; deoxyribonucleic acid, an antisense nucleotide or another agent for molecular genetic intervention; methotrexate or another antimetabolite or antiproliferative agent; dexamethasone, dexamethasone sodium phosphate, dexamethasone acetate or another dexamethasone derivative, or another anti-inflammatory steroid or non-steroidal anti-inflammatory agent; tripodal (aPDGF antagonist), angiopeptin (a growth hormone antagonist), angiogenin or other growth factors, or an anti-growth factor antibody, or another growth factor antagonist; dopamine, bromocriptine mesylate, pergolide mesylate or another dopamine agonist; 60Co, 192Ir, 32P, 111In, 90Y, 99mTc or another radiotherapeutic agent; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alpha tocopherol, superoxide dismutase, deferoxamine, a 21-amino steroid (lasaroid) or another free radical scavenger, iron chelator or antioxidant; a 14C-, 3H-, 131I-, 32P- or 36S-radiolabelled form or other radiolabelled form of any of the foregoing; estrogen or another sex hormone; AZT or other antipolymerases; acyclovir, famciclovir, rimantadine hydrochloride, ganciclovir sodium or other antiviral agents; 5-aminolevulinic acid, meta-tetrahydroxyphenylchlorin, hexadecaflouoro zinc phthalocyanine, tetramethyl hematoporphyrin, rhodamine 123 or other photodynamic therapy agents; an IgG2 Kappa antibody against *Pseudomonas aeruginosa* exotoxin A and reactive with A431 epidermoid carcinoma cells, monoclonal antibody against the noradrenergic enzyme dopamine betahydroxylase conjugated to saporin or other antibody target therapy agents; enalapril or other prodrugs; any endothelium progenitor cell attracting, binding and/or differentiating agents, including suitable chemoattractive agents and suitable polyclonal and monoclonal antibodies; cell migration inhibiting agents, such as smooth muscle cell migration inhibitors, such as Bamimistat, prolylhydrolase inhibitors, Probacol, c-proteinase inhibitors, halofuginone, and other suitable migration inhibitors; and gene therapy agents, and a mixture of any of these.

Two or more bioactives can be used when preparing a solution 102 for use in the method 100. For example, FOLFIRI, folinic acid with fluorouracil and irinotecan, is suitable for use as the bioactive in the methods and medical devices described herein. Also, FOLFOX, folinic acid with fluorouracil and oxaliplatin, is suitable for use as the bioactive in the methods and medical devices described herein.

Furthermore, the solution can be prepared in any suitable manner. Accordingly, any suitable fluid or fluids can be used when preparing the solution. A skilled artisan will be able to select an appropriate fluid for a method according to a particular method based on various considerations, including the nature of the bioactive or bioactives being used in the method. Examples of suitable fluids include water, such as Sterile Water for Injection USP, and alcohols, including ethanol and other alcohols. Also, any suitable techniques, processes, or steps can be used when preparing the solution, including heating, stirring, cooling, mixing and other suitable techniques, processes and steps.

One or more excipients can be included in the solution if desired. If included, any suitable excipient can be included, including sugars and inorganic compounds.

Any suitable substrate can be used when placing the solution over a substrate 104. A skilled artisan will be able to select an appropriate substrate for a method according to a particular embodiment based on various considerations, including the nature of the bioactive or bioactives being used in the method, the nature of the fluid or fluids used in preparing the solution comprising the bioactive or bioactives, and the point of treatment at which the medical device made by the method is intended to be used. Examples of suitable substrates include natural materials, including tissue and tissue-derived materials, and synthetic materials, including polymeric materials, and combinations of natural and synthetic materials.

Examples of suitable materials for use as the substrate include resorbable materials and non-resorbable material, bioabsorbable materials, and bioremodelable materials. Examples of suitable bioremodelable materials include extracellular matrix (ECM) materials, such as small intestine submucosa (SIS), and other bioremodelable materials, such as bovine pericardium. Other examples of suitable ECM materials that can be used include stomach submucosa, liver basement membrane, urinary bladder submucosa, tissue mucosa, and dura mater. Other examples of suitable natural materials include renal capsule matrix, abdominal fascia, and natural valve leaflets with or without adjacent vessel wall. Pleura is also considered a suitable natural material, including visceral pleura. Fixed tissues are also considered suitable, including fixed SIS, fixed pericardium and any other suitable fixed natural tissue. When fixed tissue is used, any suitable fixation technique and/or procedure can be used, including chemical fixatives, such as aldehydes, e.g., formaldehyde, gluteraldehyde, and formalin, and carbodiimides, such as ethyl dimethylaminopropyl carbodiimide, dicyclohexylcarbodiimide. Physical fixation techniques and/or procedures can also be used, including exposure to heat and/or radiation. Lyophilized preparations and chemically-dried preparations of these natural materials are also considered suitable. Examples of suitable synthetic materials include polymeric materials, such as expanded polytetrafluoroethylene, polyurethane, polyurethane urea, polycarbonate, and polyesters.

A material that defines a plurality of cells, such as a foam, is considered particularly advantageous for use as the substrate at least because the cells provide chambers for holding the solution comprising the bioactive. Both open-cell and closed-cell materials are considered suitable. Expanded collagenous materials, such as expanded extracellular matrix materials, are also considered suitable. Expanded extracellular matrix materials derived from a decellularized tissue layer are also considered suitable. For example, expanded small intestine submucosa (eSIS), which is an expanded extracellular matrix material derived from a decellularized layer of submucosa, is considered particularly suitable for use in the inventive methods and medical devices, including the examples described herein. Composite extracellular matrix materials including expanded collagenous materials in combination with non-expanded collagenous materials are also considered suitable. United States Published Patent Application No. 2009/0318934 to Johnson for COMPRESSIBLE/EXPANDABLE MEDICAL GRAFT PRODUCTS, AND METHODS FOR APPLYING HEMOSTASIS describes several materials suitable for use as the substrate and is incorporated into this disclosure, in its entirety, for the purpose of describing example materials suitable for use as the substrate in the inventive methods and medical devices. United States Published Patent Application No. 2009/0326577 to Johnson for PHYSICALLY MODIFIED EXTRACELLULAR MATRIX MATERIALS AND USES THEREFORE describes several materials suitable for use as the substrate and is incorporated into this disclosure, in its entirety, for the purpose of describing example materials suitable for use as the substrate in the inventive methods and medical devices. U.S. Pat. No. 8,741,354 to Johnson for COMPOSITE EXTRACELLULAR MATRIX MATERIALS AND MEDICAL PRODUCTS FORMED THEREFROM describes several materials suitable for use as the substrate and is incorporated into this disclosure, in its entirety, for the purpose of describing example materials suitable for use as the substrate in the inventive methods and medical devices. U.S. Pat. No. 8,329,219 to Farrell, et al. for METHODS OF PRODUCTING ECM-BASED MATERIALS describes several methods for forming materials suitable for use as the substrate and is incorporated into this disclosure, in its entirety, for the purpose of describing example methods for forming materials suitable for use as the substrate in the inventive methods and medical devices.

The substrate can have any suitable physical properties. For example, the substrate can be rigid or flexible. A flexible substrate is considered advantageous at least because it allows for physical manipulation of the medical device made by the method during use.

Furthermore, the substrate can have any suitable size, shape and configuration. A skilled artisan will be able to select an appropriate size, shape and configuration for a substrate for use in a particular method according to various considerations, including the point of treatment at which the medical device made by the method is intended to be used. The size of a particular substrate can be the size of the final medical device made by the method, or larger than the medical device. In these example methods, an optional step of folding the substrate to produce the final medical device or an optional step of subdividing the substrate into separate portions, not attached to each other and each of which comprises a final medical device, can be included. Example shares for the substrate include, but are not limited to, square, rectangular, circular, spherical, cuboid, triangular, irregular polygonal, and other suitable shapes.

FIGS. 2 and 3 illustrate an example substrate 200 suitable for use in the method 100 of making a medical device for delivering a bioactive to a point of treatment. The substrate 200 is a section of eSIS having a top surface 202, a bottom surface 204, a series of side surfaces 206, 208 (others not illustrated in FIGS. 2 and 3). The top 202 and bottom 204 surfaces are generally square-shaped, with the side surfaces 206, 208 extending between the top 202 and bottom 204 surfaces.

The substrate 200 defines a plurality of cells 220, each of which provides a chamber that has a substantially uniform composition, with variability among discrete positions within the substrate 200 provided by variability in the cells defined by the substrate 200. It is noted that the cells 220 are illustrated schematically as circles, which may or may not be representative of actual size, location, number and configuration. Also, while the cells 220 are illustrated as being uniform, it is noted that a substrate having non-uniform cells, including cells of different sizes, shapes and/or configurations, can be used.

Any suitable technique and/or process can be used when placing the solution over the substrate 104. For example, the solution can be placed within a suitable container, such as a beaker, flask, titration flask, test tube, pouch, or other suitable container, and then held over the substrate manually or through connection to an apparatus adapted to hold the vessel over the substrate, such as a stand, arm, or other apparatus. To facilitate initiating flow of the solution toward the substrate 106, described below, the container advantageously includes structure adapted to selectively allow flow of the solution out of the container, such as a valve, stopcock, or other suitable structure. In one example, the solution is placed within a pouch having an exit passageway and a valve that selectively permits and prevents the solution from exiting the pouch through the exit passageway.

FIG. 4 illustrates an example setup that can be used for placing the solution over the substrate 104 and initiating flow of solution toward the substrate 106. In this setup, a container 300 having an outer wall 302 and defining an interior chamber 304 is positioned above the substrate 200. A conventional container-holding apparatus is used to hold the container 300 above the substrate 200, but is not illustrated in FIG. 3 for simplicity. The solution 306 is placed within the interior chamber 304 of the container 300. The bioactive 308 is contained within the solution 306. It is noted that the bioactive is shown as discrete particles for illustration purposes only; the bioactive may of course not be visible in a solution used in a particular method.

The substrate 200 is the substrate illustrated in FIGS. 2 and 3. As such, the substrate has a top surface 202, a bottom surface 204, and a series of side surfaces 206, 208 (others not illustrated in FIGS. 2 and 3). The plurality of cells is not shown in FIG. 4 solely to simplify illustration.

The container 300 defines an opening 310 that is positioned immediately over the substrate 200 and that permits the solution 306 to exit the interior chamber 304 and flow toward the substrate 200. The opening 310 can have any suitable size, configuration and shape, and can include additional structure that permits selective opening and closing of the opening 310, such as a valve, removable seal, removable plug 311 or other means for regulating flow of fluid through the opening 310.

Any suitable technique or process can be used for initiating flow of the solution toward the substrate such that a portion of the solution contacts the substrate 106. A skilled artisan will be able to determine an appropriate technique or process for a particular method based on various considerations, including the structure of the container used in the method and the desired rate of flow of the solution toward the substrate. In the setup illustrated in FIG. 4, initiating flow of the solution toward the substrate 106 has been accomplished by removing removable plug 311 from opening 310 such that the solution 306 begins to flow toward the substrate 200. Furthermore, the opening 310 is configured such that the solution 308 flows toward the substrate in a column of droplets 312, each illustrated as comprising the bioactive 308 as a portion of the solution 306. In performing a particular method, with a particular solution and a particular substrate, a skilled artisan will be able to determine an appropriate flow rate for the solution, and the presence of individual droplets may or may not be considered necessary or advantageous. As described in detail below, a flow rate that produces individual droplets 312 may be advantageous in methods that include an optional massaging step.

As the solution 306 flows toward the substrate 200, the portion of the solution contacting the substrate 200 is absorbed by the substrate 200 such that a portion of the substrate 314 contains the portion of the solution 306. As flow continues, the perimeter 316 of the portion 314 gradually expands outward toward the edges of the substrate 200, which may allow for visual inspection of the method. Maintaining flow of the solution toward the substrate 108 is performed for an amount of time sufficient to achieve a desired volume of the solution 306 within the substrate 200. The amount of time for a particular method, solution and/or substrate can be determined based on a variety of factors, including a known or expected flow rate of the solution of out the vessel, a known or expected absorption capacity of the substrate, and/or a desired nominal time of exposure of solution 306 to the substrate 200.

FIG. 5 illustrates a medical device 400 made by the method 100 illustrated in FIG. 1. The medical device 400 is shown immediately after performance of the step of maintaining flow of the solution toward the substrate 108 has stopped. That is, the medical device 400 is shown as it exists after the period of time for which the maintaining flow 108 was performed. The medical device 400 includes the substrate 200 and the solution 306 comprising the bioactive 308. The solution 306, and thus the bioactive 308, is distributed substantially evenly throughout the material of the substrate 200 such that portions of the solution 306 and bioactive 308 is disposed within the cells 220 of the substrate 200. Other portions of the solution are disposed in the interstitial spaces between the cells 220. The medical device 400 can be used immediately, as described in greater detail below, or packaged for later use. For example, an optional step of placing the medical device in a pouch or other suitable container can be included.

Figure 6:
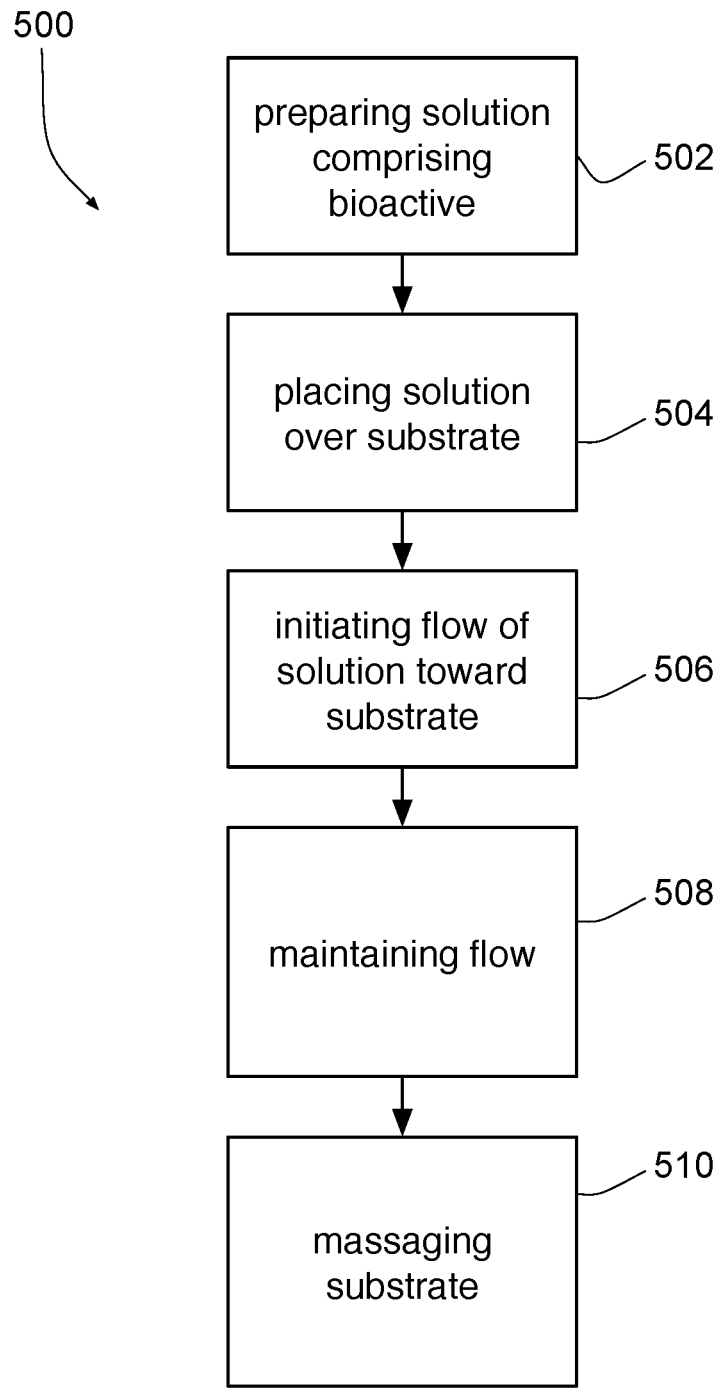
FIG. 6 is a schematic illustration of another example method of making a medical device for delivering a bioactive to a point of treatment.

FIG. 6 schematically illustrates a second example method 500 of making a medical device for delivering a bioactive to a point of treatment. This method is similar to the method 100 illustrated in FIG. 1 and described above, except as specified below. Thus, the method 500 comprises preparing a solution comprising a bioactive 502; placing the solution over a substrate 504; initiating flow of the solution toward the substrate such that a portion of the solution contacts the substrate 506; and maintaining flow of the solution toward the substrate for an amount of time sufficient to achieve a desired volume of the solution within the substrate 508.

This method 500 also includes a step of massaging the substrate 510 to distribute the solution and the bioactive throughout the substrate. The massaging is a physical manipulation of the substrate and can be performed using any suitable technique, method and/or apparatus for physically manipulating the substrate to achieve the desired distribution of the solution throughout the substrate.

Figure 7:
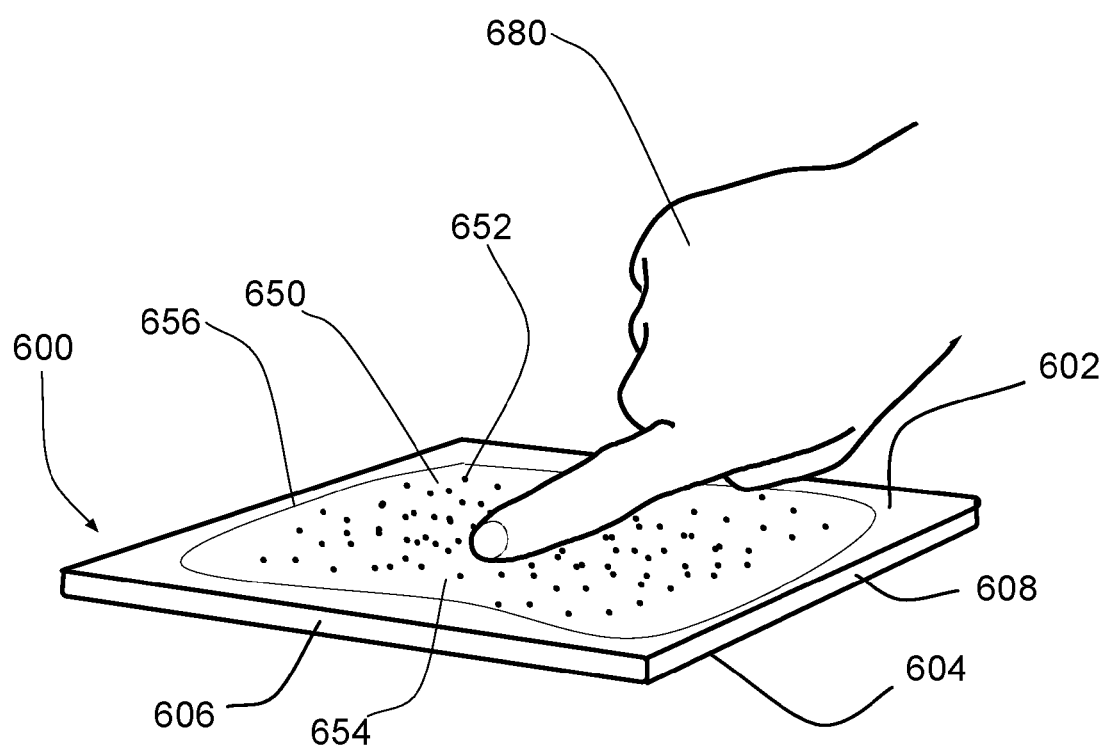
FIG. 7 is a perspective view of a substrate during performance of the massaging step of the example method illustrated in FIG. 6.

FIG. 7 illustrates an example technique for performing the step 510 of massaging the substrate. In FIG. 7, a substrate 600 has already been exposed to flow of a solution containing a bioactive and the flow has already been maintained for an amount of time sufficient to achieve a desired volume of the solution within the substrate. As such, the substrate 600 contains a desirable portion of the solution 650, which contains a desirable amount of the bioactive 652. The portion of the solution 650, however, has not been distributed throughout the substrate 600. As illustrated in FIG. 7, only a portion 654 of the substrate 600 contains the portion of the solution 650, leaving a perimeter 656. The portions of the substrate 600 that lie outside of the perimeter 656 contain no portion of the solution and, as a result, none of the bioactive. Portions of the top surface 602 and bottom surface 604 contain none of the solution and none of the bioactive 652. Indeed, the entire perimeter of the substrate 600, including side surfaces 604, 606 (and other side surfaces not visible in FIG. 7), has not been exposed to the solution 650 or the bioactive 652.

Performance of the massaging step 510 facilitates distribution of the solution 650 and the bioactive 652 throughout the substrate and can be critical to when it is desired to produce a medical device having an even or substantially even distribution of a bioactive throughout the medical device, as described below. In FIG. 7, an individual performing the method 500 is contacting the portion 654 of the substrate 600 that contains the solution with a finger of a gloved hand 680 and is moving the finger across the top surface 602 of the substrate 600 toward side surface 608 of the substrate while maintaining contact between the finger and the substrate 600. This physical manipulation of the substrate 600 distributes the solution 650 throughout the substrate 600 and can continue to be performed until the solution 654 is evenly or substantially evenly distributed throughout the substrate 600. Alternatively, the massaging step 510 can be performed by contacting a portion of the substrate that contains the solution with a mechanical apparatus, such as a roller, a pair of rollers, or another suitable mechanical apparatus, and initiating relative movement between the mechanical apparatus and substrate while maintaining contact between the substrate and mechanical apparatus.

The massaging step 510 can be performed after all other steps have been completed, as illustrated in FIG. 7, or while the step 508 of maintaining flow of the solution toward the substrate is being performed. Performing the step 510 after all other steps have been completed is considered advantageous at least because it avoids the possibility of interfering with flow of the solution toward the substrate by the presence of any item, such as a gloved hand, near the substrate.

Figure 8:
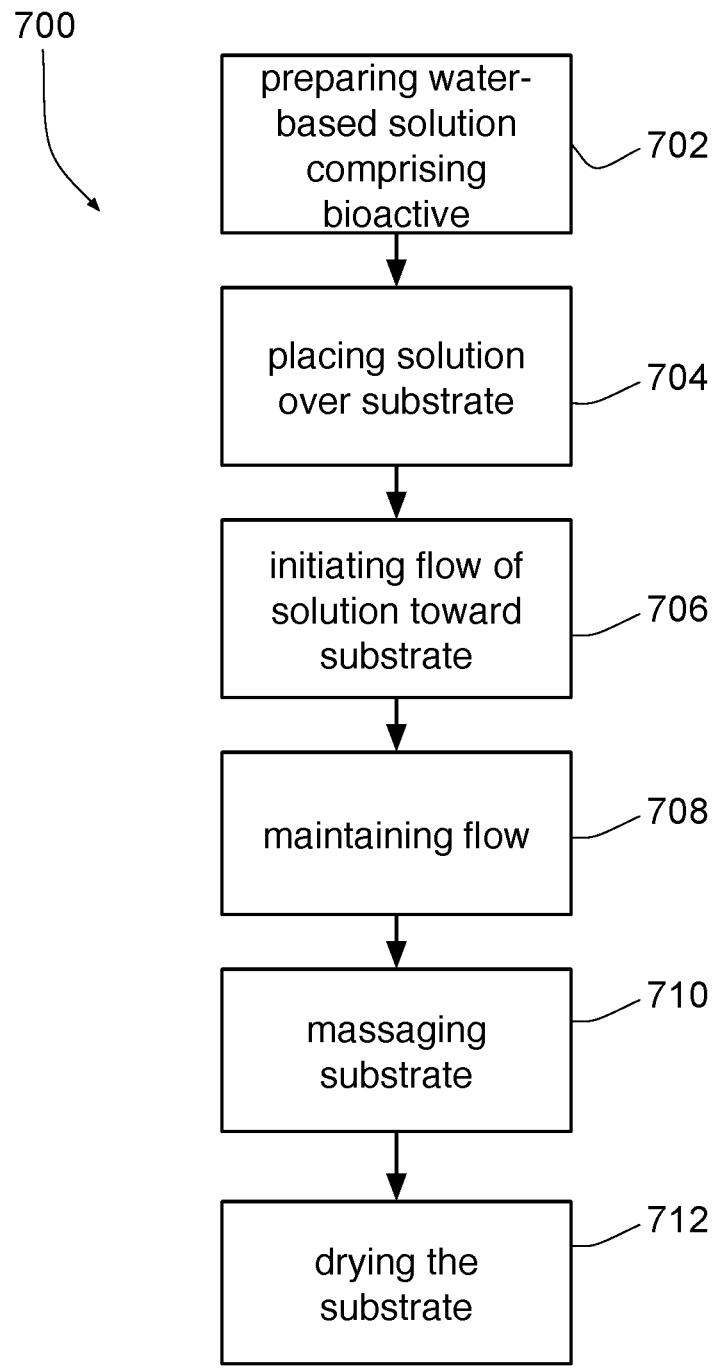
FIG. 8 is a schematic illustration of another example method of making a medical device for delivering a bioactive to a point of treatment.

FIG. 8 schematically illustrates a third example method 700 of making a medical device for delivering a bioactive to a point of treatment. This method is similar to the method 500 illustrated in FIG. 6 and described above, except as specified below. Thus, the method 700 comprises preparing a solution comprising a bioactive 702; placing the solution over a substrate 704; initiating flow of the solution toward the substrate such that a portion of the solution contacts the substrate 706; maintaining flow of the solution toward the substrate for an amount of time sufficient to achieve a desired volume of the solution within the substrate 708, and massaging the substrate 710 to distribute the solution and the bioactive throughout the substrate.

This method 700 also includes drying the substrate 712. The drying step 712 is performed to partially or fully remove the liquid portion of the solution while retaining the bioactive in the substrate. The drying step 712 can be performed using any suitable technique, method and/or apparatus for drying the substrate to achieve the desired removal of the liquid portion of the solution from the substrate. Inclusion of a drying step is considered advantageous for methods in which an aqueous solution is used, particularly with substrates that define a plurality of cells as it can reduce or eliminate trapped water that can lead to localized fluctuations in concentrations and/or release profiles of the bioactive in a medical device produced by the method.

FIG. 8 illustrates an example technique for performing the step 510 of massaging the substrate. In FIG. 8, a substrate 800 has already been exposed to flow of a solution containing a bioactive and the flow has already been maintained for an amount of time sufficient to achieve a desired volume of the solution within the substrate. As such, the substrate 800 contains a desirable portion of the solution 850, which contains a desirable amount of the bioactive 852. Furthermore, the substrate 800 has already been massaged such that the solution 850 and the bioactive 852 are distributed throughout the substrate 800. Thus, unlike the substrate 600 illustrated in FIG. 7, the substrate 800 in FIG. 9 does not have a perimeter beyond which the substrate 800 includes no solution 850 or bioactive 852. The solution 850 and bioactive 852 are substantially evenly distributed throughout the substrate 800 such that all portions of the substrate 800, including the top surface 802, bottom surface 804, and side surfaces 806, 808 (and others not illustrated in FIG. 9) include substantially similar amounts of the solution 850 and the bioactive 852.

Figure 9:
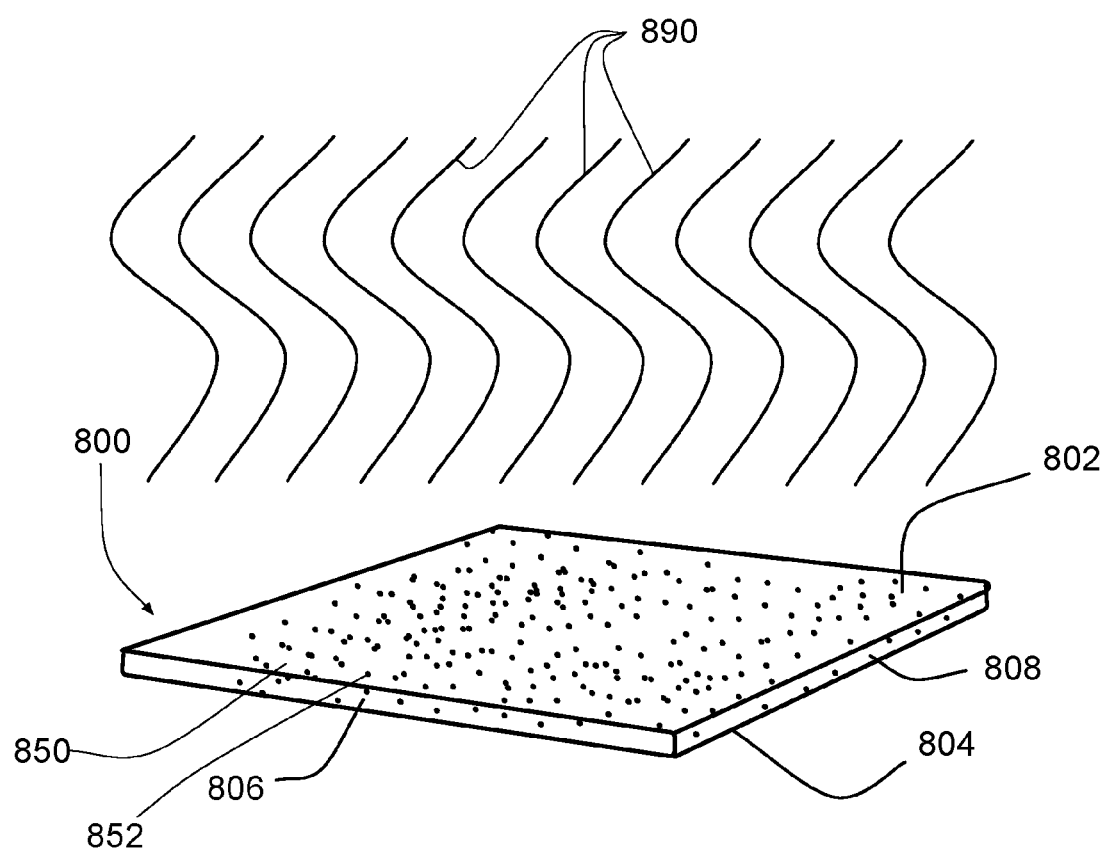
FIG. 9 is a perspective view of a substrate during performance of the drying step of the example method illustrated in FIG. 8.

Performance of the drying step 712 facilitates removal of the liquid portion of the solution 850 and can enhance retention of the bioactive 852 in and on the substrate 800. In FIG. 9, the drying step 712 is being performed. The substrate 800 has been placed in a relatively warm environment, represented by waves 890. That is, the substrate 800 has been placed in an environment having a temperature that is higher than the temperature at which at least one other step of the method 700 was performed. The drying step 712 can be performed at any suitable temperature and for any suitable length of time. A skilled artisan will be able to select an appropriate length of time and temperature for a drying step of a particular method based on various considerations, including the nature of the liquid portion of the solution, the nature of the bioactive, and the nature of the substrate.

The drying step 712 can be performed after all other steps have been completed, as illustrated in FIG. 9, or while one or more steps are being performed. For example, the drying step 712 can be performed concurrently with one or both of the steps 708 of maintaining flow of the solution toward the substrate and the step 710 of massaging the substrate. Performing the drying step 712 after all other steps have been completed is considered advantageous at least because it avoids the necessity of performing other steps within the environment having an elevated temperature. The drying step 712 can also be performed after the massaging step 710 has been completed.

Figure 10:
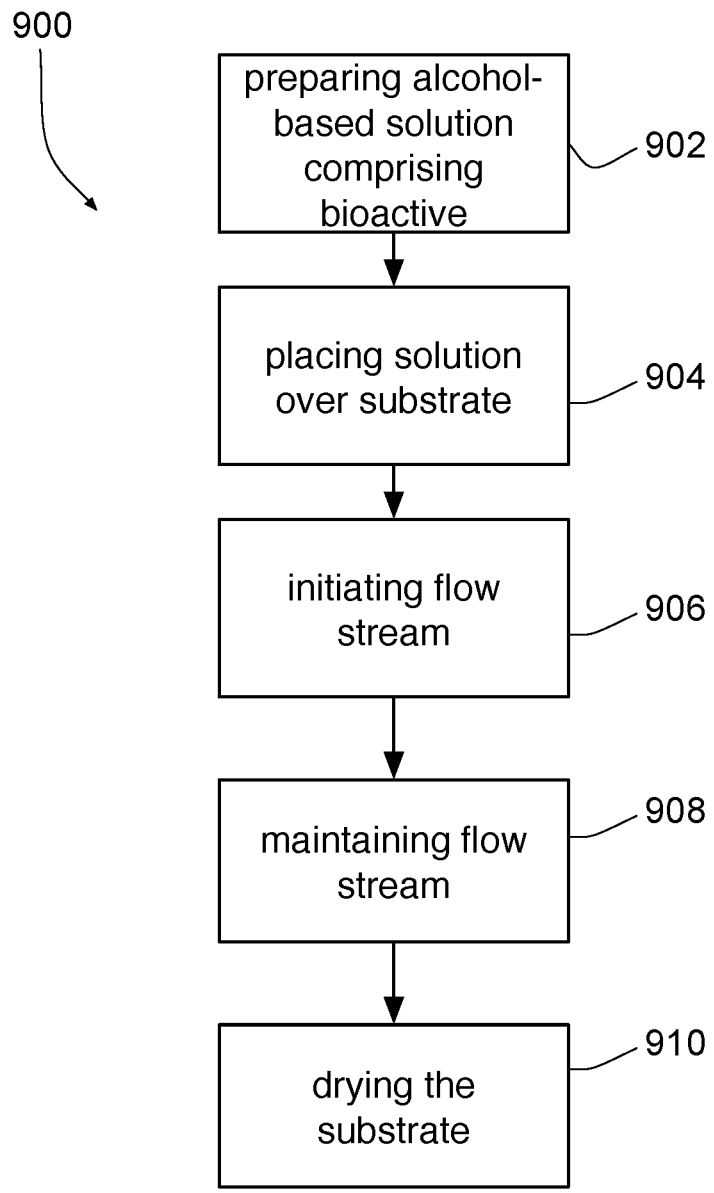
FIG. 10 is a schematic illustration of another example method of making a medical device for delivering a bioactive to a point of treatment.

FIG. 10 schematically illustrates a fourth example method 900 of making a medical device for delivering a bioactive to a point of treatment. This example method 900 is similar to the method 700 illustrated in FIG. 8 and described above, except as specified below. Thus, the method 900 comprises preparing a solution comprising a bioactive 902; placing the solution over a substrate 904; initiating flow of the solution toward the substrate such that a portion of the solution contacts the substrate 906; maintaining flow of the solution toward the substrate for an amount of time sufficient to achieve a desired volume of the solution within the substrate 908, and drying the substrate 910.

In this method, the preparing a solution 902 comprises preparing an alcohol-based solution comprising a bioactive. Thus, in this method, the liquid component of the solution comprises an alcohol. Any suitable alcohol can be used, and a skilled artisan will be able to select an appropriate alcohol for a particular method based on various considerations, including the nature of the bioactive and its relative solubilities in various alcohols. Examples of suitable alcohols include ethanol and other alcohols.

In contrast to the method 700 illustrated in FIG. 8, this method 900 does not include a step of massaging the substrate. The inventors have determined that alcohol-based solutions distribute through particular substrates effectively without need for physical manipulation. Accordingly, in methods in which the solution is an alcohol-based solution, the massaging step can be omitted.

It is noted that, in all methods, individual steps can be performed in any suitable order. For example, in a method that includes a step of massaging the substrate, the massaging step can be performed during the step of initiating flow of the solution toward the substrate, after completion of the step of initiating flow of the solution toward the substrate, or repeatedly and alternatively with several steps of initiating flow of the solution toward the substrate.

The inventors have determined that inclusion of a step of massaging the substrate is important when the solution is a water-based solution, particularly when used with a substrate comprising a natural material. For example, the inventors have determined that alcohol-based solutions distribute throughout a substrate comprising an expanded bioremodelable material, such as eSIS, relatively easily and completely following simple contact with the substrate, such as after a step of initiating flow of such a solution toward the substrate. Water-based solutions, however, do not distribute throughout such substrates as easily, and a massaging step is critical to achieving an even distribution of the solution, and the bioactive, throughout the substrate. Without the massaging step, the solution, and the bioactive, might be unevenly distributed throughout the substrate, which may make treatment procedures using the resulting medical device unpredictable.

All inventive methods, including the example methods described herein, can include additional steps if desired. For example, a method can include applying a polymer or other material onto the substrate after initiating flow of the solution toward the substrate and maintaining flow of the solution toward the substrate. In these methods, any suitable technique or process can be used for applying the polymer or other material on the substrate, such as manually spreading the polymer or other material onto the substrate, spray coating the polymer or other material onto the substrate, and dipping the substrate into a solution containing the polymer or other material. The inventors have determined that it is particularly advantageous to include applying a polymer or other material onto the substrate in methods in which the bioactive agent comprises a hydrophilic agent, as these agents tend to exit the substrate relatively quickly and the presence of a polymer or other material can delay this effect. A biodegradable, alcohol soluble polymer, such as poly (lacti-co-glycolic acid), is considered particularly advantageous for use in methods that include this optional step at least because of its well-characterized nature. If included, the inventors have determined that it is advantageous to perform the applying such that the entire external surface of the substrate is covered by the polymer or other material being used in the applying step. Also advantageously, if included, this step is performed after the bioactive has been absorbed into the substrate. Also, for methods that include a massaging step, this step is advantageously performed after completion of that step. Also, for methods that include a drying step, this step is advantageously performed after completion of that step.

The methods described herein provide flexibility in the performance of treatment procedures. The methods can be performed in anticipation of performance of a treatment procedure on a patient that uses a medical device made by the method. For example, a pharmacy can perform a particular method to prepare a medical device for use in the treatment procedure hours, days or even weeks before the treatment procedure is to be performed. The medical device made by the method can be stored in suitable packaging and made available at the time of the treatment procedure. Also, the methods can be performed immediately prior to performance of a treatment procedure on a patient that uses a medical device made by the method. Indeed, the methods described herein can be performed bedside in a hospital, immediately before use of the resulting medical device on a particular patient. In cancer treatment procedures, for example, this allows a caregiver to select a desired chemotherapeutic bioactive or immunotherapeutic bioactive for local delivery for a particular patient and then perform a method of making a medical device, such as one of the methods described herein, or instruct another to perform a method of making a medical device, and then use the resulting medical device in the immediate treatment for the particular patient.

The invention also includes the medical devices made by performance of the methods described herein. One example medical device comprises a medical device made by a method of making a medical device for delivering a bioactive, the method comprising preparing a suitable solution comprising the bioactive; placing a vessel containing the solution over a substrate comprising a biocompatible foam defining a plurality of cells; initiating flow of the solution from the vessel and toward the substrate such that the solution exits the vessel and contacts the substrate; and maintaining flow of the solution for an amount of time sufficient to achieve a desired volume of the solution within the substrate.

Another example medical device comprises a medical device made by a method of making a medical device for delivering a bioactive, the method comprising preparing a suitable water-based solution comprising the bioactive; placing a vessel containing the solution over a substrate comprising a biocompatible foam formed of an expanded natural material and defining a plurality of cells; initiating flow of the solution from the vessel and toward the substrate such that the solution exits the vessel and contacts the substrate; massaging the substrate to facilitate entry of the solution into the substrate; and maintaining flow of the solution for an amount of time sufficient to achieve a desired volume of the solution within the substrate.

Another example medical device comprises a medical device made by a method of making a medical device for delivering a bioactive, the method comprising preparing a suitable water-based solution comprising the bioactive; placing a vessel containing the solution over a substrate comprising a biocompatible foam formed of expanded small intestine submucosa and defining a plurality of cells; initiating flow of the solution from the vessel and toward the substrate such that the solution exits the vessel and contacts the substrate; massaging the substrate to facilitate entry of the solution into the substrate; maintaining flow of the solution for an amount of time sufficient to achieve a desired volume of the solution within the substrate; and drying the substrate.

While the medical devices described herein are considered useful independent of additional components, as devices for delivering a bioactive to a point of treatment, for example, other components and or functionalities can be added to provide new and useful medical devices of various types.

While various example methods and medical devices made by the methods are described with reference to specific features of particular drawings, it is understood that the various steps, elements and/or features described herein in connection with one particular example can be combined with those of another without departing from the scope of the invention. Furthermore, the methods and medical devices described and illustrated herein provide examples of the invention, and are not intended to limit the scope of the invention in any manner. Rather, they serve only to aid those skilled in the art to perform, make and use the invention.

I claim:

1. A method of making a medical device for delivering a bioactive, said method comprising:
    preparing a suitable water-based solution comprising said bioactive;
    placing a vessel containing the solution over a substrate comprising a biocompatible foam formed of an expanded natural material and defining a plurality of cells;
    initiating flow of the solution from the vessel and toward the substrate such that the solution exits the vessel and contacts the substrate;
    massaging the substrate to facilitate entry of the solution into the substrate; and maintaining flow of the solution for an amount of time sufficient to achieve a desired volume of the solution within the substrate.

2. The method of claim 1, wherein the substrate comprises a biocompatible foam formed of an expanded collagenous material.

3. The method of claim 1, wherein the substrate comprises a biocompatible foam formed of an expanded extracellular matrix material.

4. The method of claim 1, wherein the substrate comprises a biocompatible foam formed of expanded small intestine submucosa.

5. The method of claim 1, wherein the massaging the substrate comprises contacting a portion of the substrate that contains the solution with a finger and moving the finger across the substrate while maintaining contact between the finger and the substrate.

6. The method of claim 1, wherein the massaging comprises contacting a portion of the substrate that contains the solution with a mechanical apparatus and initiating relative movement between the mechanical apparatus and substrate while maintaining contact between the substrate and mechanical apparatus.

7. The method of claim 1, wherein the massaging is performed while the maintaining flow is performed.

8. The method of claim 1, wherein the massaging is performed after all other steps have been completed.

9. The method of claim 1, further comprising drying the substrate.

10. The method of claim 9, wherein the drying is performed while the massaging is being performed.

11. The method of claim 9, wherein the drying is performed after all other steps have been completed.

12. The method of claim 1, further comprising applying a polymer onto the substrate.

13. The method of claim 12, wherein the applying is performed after the massaging is completed.

14. The method of claim 13, wherein the applying comprises dipping the substrate into a solution containing the polymer.

15. The method of claim 14, wherein the applying is performed until the entire substrate is covered by the polymer.

16. A method of making a medical device for delivering a bioactive, said method comprising:
   preparing a suitable water-based solution comprising said bioactive;
   placing a vessel containing the solution over a substrate comprising a biocompatible foam formed of an expanded natural material and defining a plurality of cells;
   initiating flow of the solution from the vessel and toward the substrate such that the solution exits the vessel and contacts the substrate;
   massaging the substrate to facilitate entry of the solution into the substrate;
   maintaining flow of the solution for an amount of time sufficient to achieve a desired volume of the solution within the substrate;
   drying the substrate; and
   applying a polymer onto the substrate.

17. The method of claim 16, wherein the substrate comprises a biocompatible foam formed of an expanded collagenous material.

18. The method of claim 16, wherein the substrate comprises a biocompatible foam formed of an expanded extracellular matrix material.

19. The method of claim 16, wherein the substrate comprises a biocompatible foam formed of expanded small intestine submucosa.

20. A method of making a medical device for delivering a bioactive, said method comprising:
   preparing a suitable water-based solution comprising said bioactive;
   placing a vessel containing the solution over a substrate comprising a biocompatible foam formed of an expanded natural material and defining a plurality of cells;
   initiating flow of the solution from the vessel and toward the substrate such that the solution exits the vessel and contacts the substrate;
   massaging the substrate to facilitate entry of the solution into the substrate;
   maintaining flow of the solution for an amount of time sufficient to achieve a desired volume of the solution within the substrate;
   drying the substrate; and
   applying a polymer onto the substrate after the after the steps of massaging the substrate and drying the substrate are completed.

* * * * *